US011000592B2

(12) United States Patent
Tanner et al.

(10) Patent No.: US 11,000,592 B2
(45) Date of Patent: May 11, 2021

(54) COMPOSITIONS AND METHODS FOR TREATING NON-CORNIFIED EPITHELIAL TISSUE OF A FEMALE BODY

(71) Applicant: The Procter & Gamble Company, Cincinnati, OH (US)

(72) Inventors: Paul Robert Tanner, Lebanon, OH (US); Larry Richard Robinson, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 16/100,246

(22) Filed: Aug. 10, 2018

(65) Prior Publication Data
US 2018/0344856 A1  Dec. 6, 2018

Related U.S. Application Data

(63) Continuation of application No. 14/107,557, filed on Dec. 16, 2013, now abandoned.

(60) Provisional application No. 61/739,247, filed on Dec. 19, 2012.

(51) Int. Cl.
    A61Q 19/00    (2006.01)
    A61K 9/10     (2006.01)
    A61K 9/107    (2006.01)
    A61K 8/67     (2006.01)
    A61K 8/73     (2006.01)
    A61K 8/89     (2006.01)
    A61K 47/14    (2017.01)
    A61K 31/05    (2006.01)
    A61K 31/12    (2006.01)
    A61K 31/352   (2006.01)
    A61K 8/49     (2006.01)
    A61K 8/02     (2006.01)

(52) U.S. Cl.
    CPC ............ A61K 47/14 (2013.01); A61K 8/0208 (2013.01); A61K 8/4973 (2013.01); A61K 31/05 (2013.01); A61K 31/12 (2013.01); A61K 31/352 (2013.01); A61Q 19/005 (2013.01)

(58) Field of Classification Search
    CPC ............................ A61Q 19/005; A61P 15/02
    See application file for complete search history.

(56) References Cited

U.S. PATENT DOCUMENTS

| 3,755,560 | A  | 8/1973  | Dickert et al. |
| 4,421,769 | A  | 12/1983 | Dixon et al. |
| 5,236,986 | A  | 8/1993  | Sakuta |
| 5,387,417 | A  | 2/1995  | Rentsch |
| 5,412,004 | A  | 5/1995  | Tachibana et al. |
| 5,413,781 | A  | 5/1995  | Giwa-Agbomeirele et al. |
| 5,654,389 | A  | 8/1997  | Raleigh |
| 5,686,082 | A  | 11/1997 | N'Guyen |
| D391,162  | S  | 2/1998  | Kokenge |
| 5,725,845 | A  | 3/1998  | Krog et al. |
| 5,811,487 | A  | 9/1998  | Schulz, Jr. et al. |
| 5,837,793 | A  | 11/1998 | Harashima et al. |
| 5,993,789 | A  | 11/1999 | Bonda et al. |
| 6,113,931 | A  | 9/2000  | Bonda et al. |
| 6,126,925 | A  | 10/2000 | Bonda et al. |
| 6,159,485 | A  | 12/2000 | Yu et al. |
| 6,207,782 | B1 | 3/2001  | Czech et al. |
| 6,262,170 | B1 | 7/2001  | Kilgour et al. |
| 6,284,916 | B1 | 9/2001  | Bonda et al. |
| 6,391,863 | B1 | 5/2002  | Philippe et al. |
| 6,395,810 | B1 | 5/2002  | Luitjes |
| 6,563,012 | B2 | 5/2003  | Hill |
| 6,653,327 | B2 | 11/2003 | Majeed |
| 6,825,293 | B1 | 11/2004 | Goyal |
| 6,825,393 | B2 | 11/2004 | Roe |
| 6,872,401 | B2 | 3/2005  | Seyler et al. |
| D516,436  | S  | 3/2006  | Campbell et al. |
| D535,191  | S  | 1/2007  | Corker |
| D542,660  | S  | 5/2007  | Thomas et al. |
| D547,193  | S  | 7/2007  | Blasko et al. |
| D547,661  | S  | 7/2007  | Blasko et al. |
| 7,255,704 | B2 | 8/2007  | Hogan et al. |
| 7,262,158 | B1 | 8/2007  | Lukenbach et al. |
| 7,297,668 | B2 | 11/2007 | Johansson et al. |
| D558,591  | S  | 1/2008  | Blasko et al. |
| D563,221  | S  | 3/2008  | Ashiwa et al. |
| 7,357,919 | B2 | 4/2008  | Candau |
| D570,707  | S  | 6/2008  | Blasko et al. |
| 7,713,519 | B2 | 5/2010  | Bonda et al. |
| 7,811,342 | B1 | 10/2010 | Hsu |
| 7,947,097 | B2 | 5/2011  | You |

(Continued)

FOREIGN PATENT DOCUMENTS

EP       214641 A1    4/2010
JP    S59175408 A    10/1984

(Continued)

OTHER PUBLICATIONS

Analysis of Cosmetic Products, "Actives for skin-care products, hygiene and other toiletry products: Vitamins", (2007 edited by Amparo Salvador et al.), Elsevier B.V., pp. 371-373. (Year: 2007).*
Valenta, C. "The use of mucoadhesive polymers in vaginal delivery", Advanced Drug Delivery Reviews 57, 2005, 1692-1712. (Year: 2005).*
Anonymous: "Corn Oil (technical booklet to learn more about corn oil) ", Corn Refiners Association, XP002723333, Retrieved from the Internet: http://www.com.org/products/com-oil/, on Apr. 24, 2014, 24 pages.

(Continued)

Primary Examiner — Gina C Justice
(74) Attorney, Agent, or Firm — Melissa G Krasovec

(57) ABSTRACT

Compositions for treating non-cornified epithelial tissue of a female body, such as the labia, introitus, and the vagina are disclosed. Methods of regulating dryness in these tissues are also disclosed.

14 Claims, No Drawings

(56) References Cited

U.S. PATENT DOCUMENTS

| | | |
|---|---|---|
| 7,993,420 B2 | 8/2011 | Haerle et al. |
| 3,038,751 A1 | 10/2011 | Starling |
| 8,062,394 B2 | 11/2011 | Gaeta et al. |
| 8,217,220 B2 | 7/2012 | Berland |
| 9,295,626 B2 | 3/2016 | Pilz |
| 2002/0026165 A1 | 2/2002 | Elder et al. |
| 2003/0108492 A1 | 6/2003 | Chaudhuri |
| 2003/0157035 A1 | 8/2003 | Chaudhuri |
| 2003/0194385 A1 | 10/2003 | Gruber |
| 2003/0206943 A1 | 11/2003 | Hammons |
| 2004/0057912 A1 | 3/2004 | Bonda et al. |
| 2004/0057914 A1 | 3/2004 | Bonda et al. |
| 2004/0057916 A1 | 3/2004 | Bonda et al. |
| 2004/0062726 A1 | 4/2004 | Bonda et al. |
| 2004/0175347 A1 | 9/2004 | Bissett |
| 2004/0205226 A1 | 10/2004 | Aoki et al. |
| 2005/0214243 A1* | 9/2005 | Fleming .............. A61K 36/14 424/74 |
| 2005/0220727 A1 | 10/2005 | Lupia et al. |
| 2006/0013791 A1 | 1/2006 | Shimizu et al. |
| 2006/0034875 A1 | 2/2006 | Nakanishi et al. |
| 2006/0062816 A1 | 3/2006 | Gatto |
| 2006/0204557 A1* | 9/2006 | Gupta .............. A61K 9/0034 424/443 |
| 2006/0275237 A1 | 12/2006 | Bissett et al. |
| 2007/0020220 A1 | 1/2007 | Osborne |
| 2007/0040306 A1 | 2/2007 | Morel et al. |
| 2007/0185038 A1 | 8/2007 | Bissett et al. |
| 2007/0264224 A1 | 11/2007 | Morris et al. |
| 2007/0281033 A1 | 12/2007 | Rochat |
| 2008/0019930 A1 | 1/2008 | Candau et al. |
| 2008/0025932 A1 | 1/2008 | Bissett et al. |
| 2008/0145324 A1 | 6/2008 | Richard et al. |
| 2008/0152894 A1 | 6/2008 | Beihoffer et al. |
| 2008/0194705 A1* | 8/2008 | Ahmad ............... A61K 8/06 514/772 |
| 2009/0017080 A1 | 1/2009 | Tanner et al. |
| 2009/0018185 A1 | 1/2009 | Setchell et al. |
| 2010/0122100 A1 | 5/2010 | Strumper |
| 2010/0158824 A1 | 6/2010 | Lin |
| 2010/0172849 A1 | 7/2010 | Shaow et al. |
| 2010/0183525 A1 | 7/2010 | Lin |
| 2010/0183529 A1 | 7/2010 | Richard et al. |
| 2010/0254922 A1 | 10/2010 | Kermorvan et al. |
| 2010/0256033 A1 | 10/2010 | Menard |
| 2011/0082217 A1 | 4/2011 | Johnson |
| 2011/0117036 A1 | 5/2011 | Chaudhuri |
| 2011/0162287 A1 | 7/2011 | Cai |
| 2012/0136287 A1* | 5/2012 | Barnard .............. A61H 19/44 601/46 |
| 2013/0011346 A1 | 1/2013 | Tanner |
| 2013/0011347 A1 | 1/2013 | Tanner et al. |
| 2013/0183257 A1 | 7/2013 | Chaudhuri |
| 2013/0210867 A1* | 8/2013 | Stofman .............. A61K 31/198 514/356 |
| 2014/0078314 A1 | 3/2014 | Dowski, Jr. et al. |
| 2014/0308224 A1 | 10/2014 | Pilz |

FOREIGN PATENT DOCUMENTS

| | | |
|---|---|---|
| JP | 8173787 A | 12/1994 |
| JP | 10182435 A * | 7/1998 |
| JP | 2003012490 A | 1/2003 |

OTHER PUBLICATIONS

Synovea Doi: "A Cost-Effective Solution in Improving Skin Hydration, Barrier Homeostasis & Epidermal Architecture"; www.sytheonlld.com, retrieval date Sep. 30, 2011; 1 page.

* cited by examiner

COMPOSITIONS AND METHODS FOR TREATING NON-CORNIFIED EPITHELIAL TISSUE OF A FEMALE BODY

FIELD OF THE INVENTION

The present invention relates to absorbent articles or wipes with a personal care composition comprising an isosorbide diester as a solvent for a solid cosmetic active.

BACKGROUND OF THE INVENTION

Many personal care compositions are formulated with solid cosmetic actives that provide a benefit to the target tissue. The personal care composition can be applied to the body or clothing, and articles worn or applied against the body. The compositions can include, but are not limited to, body sprays, deodorant products (applied to the body and/or clothing (e.g., via a dryer sheet)), detersive products, fabric softeners, skin care products, hair care products, shaving compositions, and personal cleansing products (e.g., cleansing bars and body washes). The articles may include, but are not limited to, wipes, patches, and absorbent articles. Exemplary absorbent articles include diapers, feminine hygiene products, incontinence products, and wound dressings. Suitable target tissues are typically keratinous tissue including the skin, hair, nails, and the like. UV actives are used to provide such compositions with UV absorption capability. Few solid cosmetic actives are efficacious when delivered in a solid (such as a particulate) form. The solid cosmetic actives are routinely solubilized in a suitable solvent. Formulators are challenged by issues unique to personal care compositions. The solvents must be dermatologically acceptable to a wide range of consumers. The solvents ideally should maintain the solubility of the solid cosmetic active across a wide range of conditions that the compositions will encounter such as temperatures outside normal ambient conditions.

While cosmetic compositions are targeted toward improving the appearance of areas of the body that are commonly visually apparent or air exposed, there may be needs associated with non-cornified epithelial tissue of a female body, such as the labia, introitus, and the vagina (also referred to as urogenital skin). Cornified epithelial tissue is commonly associated with air exposed skin, such as the face, arm, scalp, leg, etc. whereas non-cornified epithelial tissue is commonly associated with occluded or semi-occluded skin such as the labia, introitus, urethra, inner lip, mucosal tissue, etc. By virtue of the fact that these tissues are less cornified or non-cornified, allows cosmetic ingredients and active ingredients to more easily permeate the skin and by association makes these epithelial tissues more sensitive to chemical ingredients. Cosmetic preparations that would not be irritating to cornified epithelial tissue may be very irritating to non-cornified epithelial tissue. Therefore formulators are even more challenged with regard to using solid cosmetic actives in a suitable solvent that will not compromise non-cornified epithelial tissue. The solvents ideally should maintain the solubility of the solid cosmetic active while not being irritating to the less cornified or non-cornified epithelia.

There are several conventional solvents used to solubilize solid cosmetic actives. Fatty esters of carboxylic acid such as C12-C15 alkyl bezonate are well known solvents. Esters of adipic acid such as diisopropyl adipate are another suitable class of solvents. Amide oils are another widely used class of solvents and include ethyl N-acetyl-N-butylaminoproprionate, or, more preferably, isopropyl lauroyl sarcosinate. All of these materials are well known solvents typically used by formulators in solubilizing solid cosmetic actives. However, there still exists a need for alternative solvents for solid cosmetic actives. Many of the conventions solvents have little secondary benefit in a personal care composition. A need exists for alternate solvent systems that can solubilize the solid cosmetic actives.

SUMMARY OF THE INVENTION

Personal care compositions are disclosed comprising an isosorbide diester having the formula:

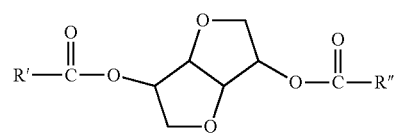

wherein R' and R" are independently selected from a straight or branched $C_{1-30}$ chain, which may be saturated or unsaturated. The personal care compositions also comprise a solid cosmetic active soluble in the isosorbide diester and a dermatologically acceptable carrier. The personal care composition may be in the form of an emulsion.

A personal care composition is also disclosed comprising an isosorbide diester having the formula:

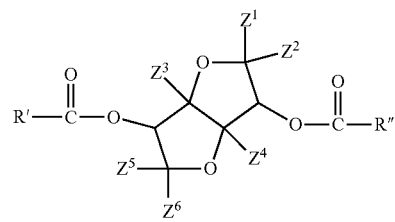

wherein R' and R" are independently selected from a straight or branched $C_{1-30}$ chain which may be saturated or unsaturated and $Z^1$-$Z^6$ are independently selected from hydrogen, hydroxyl, amino, amido, R', or R". The personal care compositions also comprise a solid cosmetic active soluble in the isosorbide diester and a dermatologically acceptable carrier. The personal care composition may be in the form of an emulsion.

Methods of making the aforementioned personal care compositions are also disclosed.

DETAILED DESCRIPTION OF THE INVENTION

The personal composition of the present invention may be used in skin care, cosmetic, and hair care products, non-limiting uses of which include moisturizers, conditioners, anti-aging compounds, skin lightening compounds, and combinations thereof. The composition is applied to keratinous tissue of the face, neck, hands, arms and other areas of the body exposed to ultraviolet radiation.

In all embodiments of the present invention, all percentages are by weight of the personal care composition, unless otherwise specified. All ratios are weight ratios, unless specifically stated otherwise. All numeric ranges are inclusive of narrower ranges. The number of significant digits conveys neither limitation on the indicated amounts nor on the accuracy of the measurements. All measurements are understood to be made at ambient conditions, where "ambient conditions" means conditions at about 25° C., under about one atmosphere of pressure, and at about 50% relative humidity.

"Personal care composition" means compositions suitable for topical application on mammalian keratinous tissue.

"Keratinous tissue" refers to keratin-containing layers disposed as the outermost protective covering of mammals which includes, but is not limited to, skin, hair, nails, cuticles, etc.

"Stable" and "stability" refer to compositions which are substantially unaltered in chemical state, physical homogeneity and/or color, upon exposure to conditions reasonably expected to be incurred in shipping, storage and use, for example, for at least 30 days at a temperature of from about 0° C. to about 40° C.

"Derivative" refers to a molecule similar to that of another one, but differing from it in respect of a certain functional moiety. Derivatives may be formed by known reactive pathways. Suitable functional moieties include esters, ethers, amides, amines, carboxylic acids, hydroxyls, halogens, thiols, and/or salt derivatives of the relevant molecule.

"Substituted" means comprising at least one heteroatomic substituent. Non-limiting examples of substituents include atoms, such as oxygen atoms and nitrogen atoms, as well as functional groups, such as hydroxyl groups, ether groups, alkoxy groups, acyloxyalkyl groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups.

"Water-insoluble" means that less than about 0.01 g of solute dissolves in 100 ml of water, at 25° C. and 1 atm of pressure and neutral pH.

The term "apply" or "application," as used in reference to a composition, means to apply or spread the compositions of the present invention onto a keratinous tissue surface.

"Dermatologically acceptable" means that the compositions or components described are suitable for use in contact with keratinous tissue, such as human skin tissue, cornified and/or non-cornified, visually commonly apparent or not visually apparent, without undue toxicity, incompatibility, instability, allergic response, and the like.

The term "leave-on," in reference to compositions, means compositions intended to be applied to and allowed to remain on the keratinous tissue. These leave-on compositions are to be distinguished from compositions which are applied to the skin and subsequently (in a few minutes or less) removed either by washing, rinsing, wiping, or the like. Leave-on compositions exclude rinse-off applications such as shampoos, facial cleansers, hand cleansers, body wash, or body cleansers. The leave-on compositions may be substantially free of cleansing or detersive surfactants. For example, "leave-on compositions" may be left on the keratinous tissue for at least 15 minutes. For example, leave-on compositions may comprise less than 1% cleansing surfactants, less than 0.5% cleansing surfactants, or 0% cleansing surfactants. The compositions may, however, contain emulsifying or other processing surfactants that are not intended to provide any significant cleansing benefits when applied topically to the skin.

I. Personal Care Composition

The present invention relates, in part, to personal care compositions comprising an isosorbide diester and a solid cosmetic active soluble in the isosorbide diester. It has been surprisingly found that the isosorbide diesters are suitable solvents for certain solid cosmetic actives. The isosorbide diesters perform as well or better than many convention solvents widely used with solid cosmetic actives in select examples.

A. Form

The personal care composition may be a skin care, anti-perspirant, deodorant, cosmetic, and hair care product. The personal care composition may have a primary use such as moisturizer, conditioner, anti-aging compound, skin lightener, sunless tanner, sunscreen, anti-perspirant, shave preparation, after-shave, foundation, lipstick, hair styling product, shampoo, cleanser, lubricant, and combinations thereof.

When the personal care products are in the form of an article, the personal care composition may be loosely employed between two or more layers/components of the article and/or adhered to a layer or component of the article with a suitable adhesive, such as, for example, a styrene-based block copolymer. The personal care products can include wipes, patches, and the like. The personal care products of the present invention can also include absorbent articles, for example, diapers, feminine hygiene products, incontinence products, and wound dressings. Feminine hygiene products can include products for menstrual fluid management or non-menstrual fluid management including but not limited to pads, pantiliners, interlabial pads, incontinence pants, and tampons. Absorbent articles typically include a liquid permeable top sheet or cover layer, a liquid impermeable back sheet or layer, and an absorbent core disposed therebetween. The articles may include additional components, such as, for example, a transfer layer underlying the top sheet that both facilitates quick fluid transfer from the top sheet to the absorbent core and deters fluid from leaving the absorbent core after the acquisition (i.e., deters "rewet" or "squeeze out"). Exemplary top sheets and transfer layers can include nonwovens, woven sheets, and apertured films. Exemplary absorbent cores can include wood pulp, hydrogels, absorbent polymers, and the like. And exemplary back sheets can include a polyolefin film. As noted above, the complexes may reside loosely between one or more of these absorbent article components and/or may be adhered to the same via an appropriate adhesive.

The topsheets of the present invention contain an effective amount of the personal care composition. As used herein, the term "effective amount of a personal care composition" refers to an amount of a particular personal care composition which, when applied to a feminine hygiene product topsheet, will be effective in transferring the personal care composition to the skin (cornified or non-cornified) of the wearer. The effective amount of a personal care composition will depend, to a large extent, on the particular personal care composition used.

As used herein, the term "wipe article" refers to a piece of material, generally non-woven material, used to cleanse body parts. In particular, most currently available wipe articles are intended for the cleaning of the peri-anal area after defecation. Other wipe articles are available for the cleansing of the face or other body parts. The present invention focuses on wipe articles for the vulvar region. Wet-wipe articles are generally of sufficient dimension to allow for convenient handling while being small enough to be easily disposed of by the sewage system or discretely disposed of in garbage bins. The material of the wipe articles is generally soft and flexible, potentially having a structured surface enhancing its cleaning performance. The material is preferably a non-woven material, generally made of synthetic compounds. However, woven materials as well as the use of natural compounds in either woven or nonwoven materials are within the scope of the present invention. The texture and material of the wipe article are of high relevance to the performance of the wipe article. In one embodiment of the present invention the non-woven material comprises fibers selected from the group consisting of polyolefin, polyester, cellulose, rayon, polyamides, polyesteramide, polyvinyl alcohols, and combinations thereof. The substrate usable for this invention can be manufactured via any suitable process, such as but not limited to, spunlace process and preferably has a dry basis weight of between about 45 grams per square meter (gsm) and 75 gsm, more preferably between 45 gsm and 65 gsm.

The size of the wipe article can vary. The wipe article can be greater than or equal to about 4 square inches (about 25 square centimeters) in size, greater than or equal to about 9 square inches (about 50 square centimeters) in size, less than or equal to about 225 square inches (about 1,450 square centimeters) in size, between about 16 square inches (about 100 square centimeters) and about 50 square inches (about 320 square centimeters), or about 35 square inches (about 225 square centimeters) in size.

The wipe article can be a cleansing wipe. The wipe article can also be a hygienic cleansing wipe that may be used by the wearer to clean menses and/or other body exudates from her body. The cleaning of menses can be particularly important because when menses leaves the wearer's body, it may tend to smear over the pudendal region of the wearer's body and be retained on the wearer's skin and pubic hair. Furthermore, the menses may then dry on the skin and in the pubic hair, and make later cleansing difficult.

Wipe articles are generally impregnated with a liquid or semi liquid composition, intended to both enhance the cleaning and to provide a smooth feeling. Generally the composition is of sufficiently low viscosity to impregnate the entire structure of the wipe article. In some other instances, the composition can be primarily present at the wipe article surface and to a lesser extent in the inner structure of the wipe article. In one optional embodiment the composition is releasably carried by the material, that is, the composition is contained either in or on a substrate and is readily releasable from the substrate by applying some force to the substrate, for example, wringing the substrate, or wiping a surface, such as a child's bottom, with the wet-wipe article.

In preparing personal care compositioned wipe articles according to the present invention, the personal care composition can be applied to the surface of the wipe article. Any of a variety of application methods that evenly distribute the personal care composition can be used. Suitable methods include spraying, printing (e.g., flexographic printing), coating (e.g., gravure coating), extrusion, or combinations of these application techniques, e.g. spraying the personal care composition on a rotating surface, such as a calender roll, that then transfers the composition to the outer surface of the topsheet.

The manner of applying the personal care composition to the surface of the wipe article can be such that the wipe article does not become saturated with the personal care composition. In another embodiment, the wipe article may be saturated with the personal care composition. Saturation of the wipe article is not required to obtain the therapeutic and/or protective personal care composition benefits. Particularly suitable application methods will apply the personal care composition primarily to the outer surface of the wipe article.

The personal care composition may involve a wide variety of forms. Non-limiting examples include simple solutions (e.g., water or oil based), dispersions, and emulsions. The personal care composition may be substantially anhydrous. "Substantially anhydrous" means that the composition comprises no more than about 1%, 0.5%, or, 0% water. The personal care compositions may be fluid or solid (gels, sticks, flowable solids, amorphous materials). In certain embodiments, the personal care composition is in the form of an emulsion. Emulsion may be generally classified as having a continuous aqueous phase (e.g., oil-in-water and water-in-oil-in-water) or a continuous oil phase (e.g., water-in-oil and oil-in-water-in-oil).

B. Isosorbide Diester

The personal care composition comprises an isosorbide diester. The isosorbide diester may have the following formula [I]:

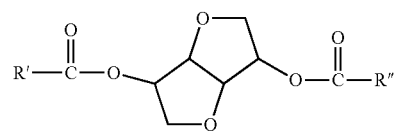

wherein R' and R" are independently selected from a straight or branched $C_{1-30}$ hydrocarbon chain, which may be saturated or unsaturated and which may be substituted. In one embodiment, R' and R" are independently selected from a straight or branched $C_{1-10}$ hydrocarbon chain, which may be saturated or unsaturated and which may be substituted. In certain embodiments, R' and R" are independently selected from a straight or branched $C_{1-30}$ or $C_{1-10}$ hydrocarbon chain, which may be saturated or unsaturated. In certain embodiments, R' and R" are independently selected from a straight or branched $C_{1-30}$ or $C_{1-10}$ hydrocarbon chain, which may be saturated. In other embodiments, R' and R" are a saturated, straight or branched $C_7$ chain. This particular embodiment has the INCI name of isosorbide dicaprylate. Isosorbide diesters of Formula I can be synthesized by know esterification techniques. For example, an isosorbide may be reacted with carboxylic acid having the desired R' or R" groups in the presence of basic or acidic catalysts under elevated pressure (100-500 kPa) and ideally elevated temperatures, for example of 120 to 220° C. Isolation may be performed by standard fractionation techniques. The isosorbide diesters may be more referred to as isosorbide diesters, In another embodiment, the personal care composition comprises an isosorbide diester that may have the following formula [II]:

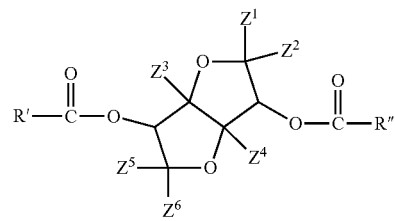

wherein R' and R" are independently selected from a straight or branched $C_{1-30}$ hydrocarbon chain, which may be saturated or unsaturated and which may be substituted; and wherein $Z^{1-6}$ are independently selected from hydrogen, hydroxyl, amino, amido, R', or R". In one embodiment, at least one of $Z^{1-6}$ is a hydroxyl group. In an alternate embodiment, $Z^1$, $Z^2$, $Z^5$, and $Z^6$ are independently selected from hydrogen, hydroxyl, amino, amido, R', or R"; and $Z^3$ and $Z^4$ are hydrogen.

The personal care composition may comprise a sufficient amount of the isosorbide diester to solubilize the solid cosmetic active, which is described in further detail below. In certain embodiments, the personal care composition comprises at least 2 parts, by weight, isosorbide diester to solubilize every 1 part, by weight, solid cosmetic active. In another embodiment, the personal care composition comprises at least 3 parts, 5 parts, 8 parts, or 10 parts, by weight, isosorbide diester to solubilize every 1 part, by weight, solid cosmetic active. In yet another embodiment, the personal care composition comprises at least 16 parts or 32, by weight, isosorbide diester to solubilize every 1 part, by weight, solid cosmetic active. In select embodiments, the personal care composition may comprise from about 0.1% to about 95% of the isosorbide diester. For example, the personal care composition may comprise 0.1%, 0.5%, 1%, 2%, 5%, 10%, 15%, 20%, 25%, 30%, 35%, 40%, 45%, 50%, 55%, 60%, 65%, 70%, 75%, 80%, or 85%, to about 90%, 85%, 80%, 75%, 70%, 65%, 60%, 55%, 50%, 45%, 40%, 35%, 30%, 25%, 20%, 15%, 10%, 5%, or 3% of the isosorbide diester.

C. Solid Cosmetic Active

The personal care composition comprises at least one solid (at ambient conditions) cosmetic active soluble in the isosorbide diester. The solid cosmetic active is solid at ambient conditions. The solid cosmetic actives may be an organic molecule. The solid cosmetic active may be water-insoluble (i.e., excluding hydrophilic actives such as water-soluble vitamins) Suitable solid cosmetic actives include: polyphenols such as flavonoids and tetrahydrocurcuminoids; hydroxyl acids; N-acyl amino acid compounds; phytosterols; hexylresorcinol; tocopherol succinate; and glycyrrhetinic acid. In order to deliver the solid cosmetic active to keratinous tissue, the solid cosmetic active may be substantially or fully dissolved, and, thus, does not remain in a solid or crystalline form in the personal care composition.

Polyphenolic compounds include flavonoids such as those broadly disclosed in U.S. Pat. No. 5,686,082. Exemplary flavonoids include one or more flavones, one or more isoflavones, one or more coumarins, one or more chromones, one or more dicoumarols, one or more chromanones, one or more chromanols, isomers (e.g., cis/trans isomers) thereof, and mixtures thereof. Suitable flavones and isoflavones include unsubstituted flavone, unsubstituted isoflavone, daidzein (7,4'-dihydroxy isoflavone), genistein (5,7,4'-trihydroxy isoflavone), equol (7,4'-isoflavandiol), apigenin (4',5,7-trihydroxyflavone), quercetin (2-(3,4-dihydroxyphenyl)-3,5,7-trihydroxy-4H-chromen-4-one), 5,7-dihydroxy-4'-methoxy isoflavone, 7,2'-dihydroxy flavone, 3',4'-dihydroxy naphthoflavone, 7,8-benzoflavone, 4'-hydroxy flavone, 5,6-benzoflavone, soy isoflavones (e.g., isoflavones extracted from soy) and other plant, fungal, or bacterialsources of such mixtures (e.g., red clover), and mixtures thereof. Other suitable flavonoids include hesperitin, hesperidin, and mixtures thereof. Other polyphenolic compounds include tetrahydrocurcuminoids. Tetrahydrocurcuminoids include tetrahydrocurcumin (i.e., INCI name tetrahydrodiferuloylmethane), tetrahydrodemethoxycurcumin (i.e., INCI name tetrahydrodemethoxydiferuloylmethane), and tetrahydrobismethoxycurcumin (i.e., INCI name tetrahydrobisdemethoxydiferuloylmethane).

Hydroxy acids include alpha- and beta-hydroxy acids. Suitable alpha-hydroxy acids include including glycolic acid, lactic acid, malic acid, citric acid, tartaric acid, and derivatives thereof. Suitable beta-hydroxy acids include salicylic acid, carnitine, and derivatives thereof.

The topical compositions of the present invention can comprise one or more N-acyl amino acid compounds. The amino acid can be one of any of the amino acids known in the art. The N-acyl amino acid compounds of the present invention can correspond to the formula:

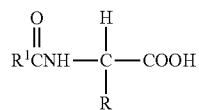

wherein R can be a hydrogen, alkyl (substituted or unsubstituted, branched or straight chain), or a combination of alkyl and aromatic groups. $R^1$ can be $C_1$ to $C_{30}$, saturated or unsaturated, straight or branched, substituted or unsubstituted alkyls; substituted or unsubstituted aromatic groups; or mixtures thereof. In certain embodiments, the N-acyl amino acid compound is selected from the group consisting of N-acyl phenylalanine, N-acyl tyrosine, their isomers, their salts, and derivatives thereof. The amino acid can be the D or L isomer or a mixture thereof. A exemplary N-acyl amino acid is N-undecylenoyl-L-phenylalanine, wherein the acyl group is a C11 mono-unsaturated fatty acid moiety and the amino acid is the L-isomer of phenylalanine. N-undecylenoyl-L-phenylalanine is commercially available under the tradename Sepiwhite® from SEPPIC.

Phytosterols can be synthetic or natural in origin and can be used as essentially pure compounds or mixtures of compounds (e.g., extracts from natural sources). Phytosterols are generally found in the unsaponifiable portion of vegetable oils and fats and are available as free sterols, acetylated derivatives, sterol esters, ethoxylated or glycosidic derivatives. Exemplary phytosterols include beta-sitosterol, campesterol, brassicasterol, delta-5-avennasterol, lupenol, alpha-spinasterol, stigmasterol, their derivatives, isomers, tautomers, and combinations thereof. These materials are commercially available from Aldrich Chemical Company (Milwaukee, Wis.) or Sigma Chemical Company (St. Louis, Mo.).

Another suitable skin care actives include hexylresorcinol, glycyrrhetinic acid, and tocopherol succinate.

The personal care composition may comprise an amount of the solid cosmetic active sufficient to provide a desired benefit. In particular embodiments, the personal care composition comprises from about 0.01% to about 20%, by weight of the composition, of a solid cosmetic active. In other embodiments, the personal care composition comprises from about 0.01%, 0.1%, 0.5%, 1%, or 2% to about 15%, 10%, 6%, 5%, or 3%, by weight of the composition, of a solid cosmetic active.

D. Carrier

The personal care composition may comprise a one or more carriers. Carriers may be selected for various stability, aesthetics, and/or compatibility with other materials present in the personal care composition.

Suitable carriers include water and/or water miscible solvents. The personal care composition may comprise from about 1% to about 95% by weight of water and/or water miscible solvent. The composition may comprise from about 1%, 3%, 5%, 10%, 15%, 20%, 25%, 30%, 35%, 40%, 45%, 50%, 55%, 60%, 65%, 70%, 75%, 80%, or 90% to about 95%, 90%, 85%, 80%, 75%, 70%, 65%, 60%, 55%, 50%, 45%, 40%, 35%, 30%, 25%, 20%, 15%, 10%, or 5% water and/or water miscible solvents. Suitable water miscible solvents include monohydric alcohols, dihydric alcohols, polyhydric alcohols, glycerol, glycols, polyalkylene glycols such as polyethylene glycol, and mixtures thereof. Particularly suitable solvents, include lower aliphatic alcohols such as ethanol, propanol, butanol, isopropanol; diols such as 1,2-propanediol, 1,3-propanediol, butanediol, pentanediol, hexanediol, heptanediol, decanediol; glycerin; water, and mixtures thereof. In certain embodiments, the personal care composition comprises water, diols, glycerin, and combinations thereof.

Suitable carriers also include oils. The personal care composition may comprise from about 0.1% to about 95% by weight of one or more oils. The composition may comprise from about 0.1%, 0.5%, 1%, 2%, 5%, 10%, 15%, 20%, 25%, 30%, 35%, 40%, 45%, 50%, 55%, 60%, 65%, 70%, 75%, 80%, 85%, or 90% to about 90%, 85%, 80%, 75%, 70%, 65%, 60%, 55%, 50%, 45%, 40%, 35%, 30%, 25%, 20%, 15%, 10%, 5%, or 3% of one or more oils. Oils may be used to solubilize, disperse, or carry materials that are not suitable for water or water soluble solvents. Suitable oils include silicones, hydrocarbons, esters, amides, ethers, and mixtures thereof. Oils may be fluid at ambient conditions. However, certain personal care product forms (i.e., solid or semi-solid stick) may require non-fluid oils. The oils may be volatile or nonvolatile. "Nonvolatile" means a material that exhibit a vapor pressure of no more than about 0.2 mm Hg at 25° C. at one atmosphere and/or a material that has a boiling point at one atmosphere of at least about 300° C. "Volatile" means that the material exhibits a vapor pressure of at least about 0.2 mm of mercury at 20° C. Volatile oils may be used to provide a lighter feel when a heavy, greasy film is undesirable.

Non-limiting examples of oils or fats such as natural oils or fats, or natural oil or fat derivatives, in particular of plant or animal origin include apricot oil, babassu oil, castor oil, coconut oil, cod liver oil, hydrogenated corn oil, hydrogenated cottonseed oil, hazelnut oil, jojoba oil, macadamia oil, meadowfoam seed oil, mink oil, maringa oil, marula oil, mortierella oil, palm kernel oil, hydrogenated peanut oil, hydrogenated rapeseed oil, rose hip oil, hydrogenated safflower oil, hydrogenated soybean oil, hydrogenated sunflower oil, hydrogenated walnut oil, hydrogenated wheat germ oil, or the hardened derivatives thereof.

Other non-limiting examples of fats and oils suitable as carriers herein include: butter, C12-C18 alkyl triglycerides, caprylic/capric/lauric triglyceride, caprylic/capric/linoleic triglyceride, caprylic/capric/stearic triglyceride, caprylic/capric triglyceride, cocoa butter, C10-C18 alkyl triglycerides, egg oil, epoxidized soybean oil, glyceryl triacetyl hydroxystearate, glyceryl triacetyl ricinoleate, glycosphingolipids, hydrogenated castor oil, hydrogenated castor oil laurate, hydrogenated coconut oil, hydrogenated C12-C18 alkyl triglycerides, hydrogenated fish oil, hydrogenated lard, hydrogenated menhaden oil, hydrogenated mink oil, hydrogenated orange roughy oil, hydrogenated shark liver oil, hydrogenated tallow, hydrogenated vegetable oil, lanolin and lanolin derivatives, lanolin alcohol, lard, lauric/palmitic/oleic triglyceride, lesquerella oil, maleated soybean oil, neatsfoot oil, oleic/linoleic triglyceride, oleic/palmitic/lauric/myristic/linoleic triglyceride, oleostearine, olive husk oil, omental lipids, pengawar djambi oil, pentadesma butter, phospholipids, shea butter, tallow, tribehenin, tricaprin, tricaprylin, triheptanoin, trihydroxymethoxystearin, trihydroxystearin, triisononanoin, triisostearin, trilaurin, trilinolein, trilinolenin, trimyristin, trioctanoin, triolein, tripalmitin, trisebacin, tristearin, triundecanoin, and the like, as well as mixtures thereof.

Suitable oils include volatile oils. In certain embodiments, the volatile oils may have a viscosity ranging from about 0.5 to 5 centistokes at 25° C. Volatile oils may be used to promote more rapid drying of the skin care composition after it is applied to skin. Nonvolatile oils are also suitable for use in the composition. Nonvolatile oils are often used for emolliency and protective properties.

Suitable oils can optionally further comprise essential oil materials. Non-limiting examples of suitable essential oil materials include Acorus gramineus, Anthemis nobilis, Artemisia dracunculus, Basil, Bergamot, Calamintha sylvatica, Caraway, Cedarwood, Chamomile, Cineol, Cinnamon, Cinnamon bark, Citrus aurantium, Clove, Cypress, Dill, Eucalyptus, Eugenol, Frankincense, Galangol, Geranium, Ginger, Hibiscus, Hop, Jasmine, Juniper, Laurus nobilis, Lavender, Lemon balm, Lemongrass, Lemon, Limonene, Linalool, Linalyl acetate, Lippia alba, Marjoram, Melissa, Myrrh, Neroli, Nutmeg, Passiflora, Patchouli, Peppermint, Pinene, Rose, Rosewood, Rosemary, Sage, Sandalwood, Spearmint, Sweet Fennel, Sweet Orange, Tea Tree, Thyme, Valerian, Ylang ylang, Zadoary, Hibiscus, or mixtures thereof. Preferred essential oils associated with arousal include Cypress, Hibiscus, Juniper, Cineol, Citrus, Sweet Orange, and Rosemary. Preferred oils associated with a harmonizing effect include Lavender, Neroli, and Ylang ylang.

The particular essential oils herein, such as described above, can be blended in a carrier at a concentration ranging from about 0.0001% to about 10.0%, from about 0.0001% to about 3.0%, from about 0.0001% to about 0.1%, from about 0.001% to about 1%, or from about 0.01% to about 1.0%, by weight of the composition. The essential oil can also be prepared in a premix in an oil material herein. Nonetheless, the final concentration of the essential oil will typically fall in the ranges described above.

Other suitable oils will include those enriched in omega-6 fatty acid. Unsaturated fatty acids, such as omega fatty acids, tend to be instable and tend to easily oxidize. Oxidation can be promoted by multiple sources that include temperature, light, air, oxygen, moisture, and metals (metals can act as catalysts). See, e.g., Belitz H-D, Grosch W, and Schieberle P, Lipids In Food Chemistry 3rd ed. Springer-Verlag, Heidelberg, 2004, p. 157-242. Indeed, common sources of product making can promote instability. For example, melting and mixing the composition ingredients can require high temperatures (to a temperature above the melting point of the lotion composition ingredients, e.g., greater than 70° C.). In order to melt and preserve the uniformity of a composition, it is common to heat the composition application tank to high temperatures (e.g., greater than 60° C., preferably above 70° C.) with mixing. Furthermore, the composition can remain in the tank for a considerable amount of time (e.g., greater than 24 hours). Another source of instability can be the shelf storage of the finished product. It is not unusual for product to remain on the shelf (in the store or at home) for at least a year, two years, or three years, and, depending on geographical location, storage temperatures can exceed 40° C. Collectively, these factors can lead to oxidation and creation of reactive oxygen-free radicals or active oxygen. This can lead to product deterioration such as discoloration (i.e., yellowing) and/or rancid odor. When in contact with the skin (cornified or non-cornified), active oxygen can damage skin barrier function.

A common measure for monitoring oxidative stability is the development of hydroperoxides (peroxide value or PV) over time. Oxidative stability can also be expressed in terms of the time required to obtain secondary oxidation products when aerating a sample at elevated temperature. A suitable measure of oxidative stability is called the Oil Stability Index (referred to herein as "OSI"). The OSI of an oil material can be measured according to the American Oil Chemical Society Oil Stability Index Method (AOCS Official Method Cd 12b-92).

In one embodiment, the oil material of the present invention is selected to have an oil stability index ("OSI") of at least about 10 hours at 110° C., at least about 14 hours at 110° C., or at least about 18 hours at 110° C.

It is believed that oil materials comprising relatively high levels of oleic acid tend to be more stable in the context of the present invention. In one embodiment, the oil material of the present invention comprises at least about 10%, from about 10% to about 80%, or from about 15% to about 70%, by weight of the oil material, of oleic acid. In one embodiment, the composition comprises from about 0.0005% to about 16%, from about 0.005% to about 12%, or from about 0.01% to about 8%, by weight of the composition, of oleic acid.

It is believed that oil materials comprising relatively low levels of linolenic acid (omega-3 fatty acid) tend to be more stable in the context of the present invention. In one embodiment, the oil material of the present invention comprises less than about 10%, from about 10% to about 5%, or from about 5% to about 0%, by weight of the oil material, of linolenic acid. In one embodiment, the composition comprises from about 2% to about 0%, from about 1% to about 0%, or from about 0.5% to about 0%, by weight of the composition, of linolenic acid.

Non-limiting examples of suitable oil materials exhibiting the desired properties described herein include oleic canola Oil (Brassica campestris, B. napus, B. rapa; characterized by having an oleic content greater than 70%, e.g., high oleic canola oil, very high oleic canola oil, or partially hydrogenated canola oil), marula kernel oil (Sclerocarya birrea), palm oil (Elaeis Guineensis Oil), palm olein, palm stearin, palm superolein, pecan oil, pumpkin seed oil, oleic safflower oil (Carthamus Tinctorius; characterized by having an oleic content of greater than about 30% and omega-6 fatty acid content of less than about 50%, e.g., high oleic safflower oil), sesame oil (Sesamum indicum, S. oreintale), soybean oil (Glycine max, e.g., high oleic soybean, low linolenic soybean oil, partially hydrogenated), oleic sunflower oil (Helianthus annus; characterized by having an oleic content of greater than about 40%, e.g., mid oleic sunflower or high oleic sunflower oil), and mixtures thereof. Oleic canola oil, palm oil, sesame oil, high oleic safflower oil, high oleic soybean oil, mid oleic sunflower oil, and high oleic sunflower oil are common plant-bred derived oils and may be also be derived from non-genetically modified organisms (non-GMO).

Non-limiting examples of oil materials are commercially-available from a number of vendors, including Cargill for partially hydrogenated soybean oil (i.e., Preference® 110W soybean oil or Preference® 300 high stability soybean oil), mid oleic sunflower oil (i.e., NuSun® mid-oleic sunflower oil), high oleic sunflower oil (i.e., Clear Valley® high oleic sunflower oil), high oleic canola oil, very high oleic canola, and partially hydrogenated low erucic rapeseed oil (i.e., Clear Valley® 65 high oleic canola oil and Clear Valley® 75 high oleic canola oil); Lambert Technology for high oleic canola oil (i.e., Oleocal C104); Arch Personal Care for manila kernel oil; Pioneer for high oleic soybean oil (i.e., Plenish®); Asoyia for low linolenic soybean oil (i.e., Ultra Low Linolenic Soybean Oil®); and Dipasa, Inc. for refined sesame oil.

It should be noted that the grade of oil material can be important as well in achieving the desired properties of the oil material as described herein. For example, the source of the oil material can be important, as the same oil (e.g. sesame oil) can exhibit a wide range of OSI values depending upon the source of the oil material.

The oil material can further comprise a blend of oils, including those described supra, as well as additional oil materials. Suitable additional oil materials can include acai berry oil, almond oil, avocado oil, beech oil, brazil nut oil, camelina sativa oil (family Brassicaceae, e.g. Camelina Sativa, Gold of Pleasure, False Flax, etc.), camellia seed oil, canola oil, carrot seed oil, cashew nut oil, caster oil, cherry kernel oil, chia oil, corn oil, cottonseed oil, hydrogenated cottonseed oil, evening primrose oil, filbert (hazelnut) oil, grapeseed oil, hemp oil, hickory nut oil, jojoba oil, kukui oil, lanolin, olive oil (Olea europaea), macadamia oil, maringa oil, meadowfoam oil, neem oil, palm kernel oil, olive oil, passionflower oil (family Passiflora, Passiflora Incarnata), peanut oil, peach kernel oil, pistachio nut oil, rapeseed oil, rice bran oil, rose hip oil, safflower oil, sorghum oil, soybean oil, sunflower seed oil, tall oil, vegetable oil, vegetable squalene, walnut oil, wheat germ oil, and mixtures thereof. The oil material of the present invention can be selected from the group consisting of camelina sativa seed oil, oleic canola oil, evening primrose oil, marula kernel oil, palm oil, palm olein, palm stearin, palm superolein, passiflora incarnata seed oil, pecan oil, pumpkin seed oil, oleic safflower oil, sesame oil, soybean oil, oleic sunflower oil, vegetable oil and mixtures thereof.

Preferred oil materials of the present invention include a mixture of vegetable oil and camelina sativa seed oil (commercially-available as Lipex® Omega 3/6 from Aarhus Karlshamn Sweden AB), a mixture of vegetable oil and passiflora incarnata seed oil (commercially-available as Lipex® Omega Passiflora from Aarhus Karlshamn Sweden AB), a mixture of vegetable oil and evening primrose oil (commercially-available as Lipex Omega EPO from Aarhus Karlshamn Sweden AB), high oleic canola oil (commercially-available as Clear Valley® 75 high oleic canola oil from Cargill), or mixtures thereof.

Suitable silicone oils include polysiloxanes. Polylsiloxanes may have a viscosity of from about 0.5 to about 1,000,000 centistokes at 25° C. Such polysiloxanes can be represented by the general chemical formula:

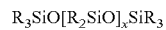

wherein R is independently selected from hydrogen or $C_{1-30}$ straight or branched chain, saturated or unsaturated alkyl, phenyl or aryl, trialkylsiloxy; and x is an integer from 0 to about 10,000, chosen to achieve the desired molecular. In certain embodiments, R is hydrogen, methyl, or ethyl. Commercially available polysiloxanes include the polydimethylsiloxanes, which are also known as dimethicones, examples of which include the DM-Fluid series from Shin-Etsu, the Vicasil® series sold by Momentive Performance Materials Inc., and the Dow Corning® 200 series sold by Dow Corning Corporation. Specific examples of suitable polydimethylsiloxanes include Dow Corning® 200 fluids (also sold as Xiameter® PMX-200 Silicone Fluids) having viscosities of 0.65, 1.5, 50, 100, 350, 10,000, 12,500 100, 000, and 300,000 centistokes.

Suitable dimethicones include those represented by the chemical formula:

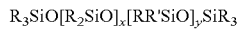

wherein R and R' are each independently hydrogen or $C_{1-30}$ straight or branched chain, saturated or unsaturated alkyl, aryl, or trialkylsiloxy; and x and y are each integers of 1 to 1,000,000 selected to achieve the desired molecular weight. Suitable silicones include phenyl dimethicone (Botansil™ PD-151 from Botanigenics, Inc.), diphenyl dimethicone (KF-53 and KF-54 from Shin-Etsu), phenyl trimethicone (556 Cosmetic Grade Fluid from Dow Corning), or trimethylsiloxyphenyl dimethicone (PDM-20, PDM-200, or PDM-1000 from Wacker-Belsil). Other examples include alkyl dimethicones wherein at least R' is a fatty alkyl (e.g., $C_{12-22}$). A suitable alkyl dimethicone is cetyl dimethicone, wherein R' is a straight C16 chain and R is methyl. Cetyl dimethicone, is available as s 2502 Cosmetic Fluid from Dow Corning or as Abil Wax 9801 or 9814 from Evonik Goldschmidt GmbH.

Cyclic silicones are one type of silicone oil that may be used in the composition. Such silicones have the general formula:

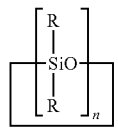

wherein R is independently selected from hydrogen or $C_{1-30}$ straight or branched chain, saturated or unsaturated alkyl, phenyl or aryl, trialkylsiloxy; and where n=3-8 and mixtures thereof. Commonly, a mixture of cyclomethicones is used where n is 4, 5, and/or 6. Commercially available cyclomethicones include Dow Corning UP-1001 Ultra Pure Fluid (i.e. n=4), Dow Corning XIAMETER® PMX-0245 (i.e. n=5), Dow Corning XIAMETER® PMX-0245 (i.e. n=6), Dow Corning 245 fluid (i.e. n=4 and 5), and Dow Corning 345 fluid (i.e. n=4, 5, and 6).

Suitable hydrocarbon oils include straight, branched, or cyclic alkanes and alkenes. The chain length may be selected based on desired functional characteristics such as volatility. Suitable volatile hydrocarbons may have between 5-20 carbon atoms or, alternately, between 8-16 carbon atoms.

Other suitable oils include esters. The suitable esters typically contained at least 10 carbon atoms. These esters include esters with hydrocarbyl chains derived from fatty acids or alcohols (e.g., mono-esters, polyhydric alcohol esters, and di- and tri-carboxylic acid esters). The hydrocarbyl radicals of the esters hereof may include or have covalently bonded thereto other compatible functionalities, such as amides and alkoxy moieties (e.g., ethoxy or ether linkages, etc.). Exemplary esters include, but are not limited to, isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, C12-15 alkyl benzoate, diisopropyl adipate, dibutyl adipate, and oleyl adipate. Other suitable esters are further described in the Personal Care Product Council's *International Cosmetic Ingredient Dictionary and Handbook*, Thirteenth Edition, 2010, under the functional category of "Esters." Other esters suitable for use in the personal care composition include those known as polyhydric alcohol esters and glycerides.

Other suitable oils include amides. Amides include compounds having an amide functional group while being liquid at 25° C. and insoluble in water. Suitable amides include N-acetyl-N-butylaminopropionate, isopropyl N-lauroylsarcosinate, isopropyl lauroylsarcosinate, and N,N,-diethyltoluamide. Other suitable amides are disclosed in U.S. Pat. No. 6,872,401.

Other suitable oils include ethers. Suitable ethers include saturated and unsaturated fatty ethers of a polyhydric alcohol, and alkoxylated derivatives thereof. Exemplary ethers include $C_{4-20}$ alkyl ethers of polypropylene glycols, and di-$C_{8-30}$ alkyl ethers. Suitable examples of these materials include PPG-14 butyl ether, PPG-15 stearyl ether, dioctyl ether, dodecyl octyl ether, and mixtures thereof.

The personal care composition may comprise an emulsifier. An emulsifier is particularly suitable when the composition is in the form of an emulsion or if immiscible materials are being combined. The skin care composition may comprise from about 0.05%, 0.1%, 0.2%, 0.3%, 0.5%, or 1% to about 20%, 10%, 5%, 3%, 2%, or 1% emulsifier. Emulsifiers may be nonionic, anionic or cationic. Non-limiting examples of emulsifiers are disclosed in U.S. Pat. No. 3,755,560, U.S. Pat. No. 4,421,769, and McCutcheon's, *Emulsifiers and Detergents*, 2010 Annual Ed., published by M. C. Publishing Co. Other suitable emulsifiers are further described in the Personal Care Product Council's *International Cosmetic Ingredient Dictionary and Handbook*, Thirteenth Edition, 2006, under the functional category of "Surfactants—Emulsifying Agents."

Suitable emulsifiers include the following classes of ethers and esters: ethers of polyglycols and of fatty alcohols, esters of polyglycols and of fatty acids, ethers of polyglycols and of fatty alcohols which are glycosylated, esters of polyglycols and of fatty acids which are glycosylated, ethers of $C_{12-30}$ alcohols and of glycerol or of polyglycerol, esters of $C_{12-30}$ fatty acids and of glycerol or of polyglycerol, ethers of oxyalkylene-modified $C_{12-30}$ alcohols and of glycerol or polyglycerol, ethers of $C_{12-30}$ fatty alcohols comprising and of sucrose or of glucose, esters of sucrose and of $C_{12-30}$ fatty acids, esters of pentaerythritol and of $C_{12-30}$ fatty acids, esters of sorbitol and/or of sorbitan and of $C_{12-30}$ fatty acids, ethers of sorbitol and/or of sorbitan and of alkoxylated sorbitan, ethers of polyglycols and of cholesterol, esters of $C_{12-30}$ fatty acids and of alkoxylated ethers of sorbitol and/or sorbitan, and combinations thereof.

Linear or branched type silicone emulsifiers may also be used. Particularly useful polyether modified silicones include KF-6011, KF-6012, KF-6013, KF-6015, KF-6015, KF-6017, KF-6043, KF-6028, and KF-6038 from Shin Etsu. Also particularly useful are the polyglycerolated linear or branched siloxane emulsifiers including KF-6100, KF-6104, and KF-6105 from Shin Etsu.

Emulsifiers also include emulsifying silicone elastomers. Suitable emulsifying silicone elastomers may include at least one polyalkyl ether or polyglycerolated unit. Polyoxyalylenated emulsifying silicone elastomers that may be used in at least one embodiment of the invention include those sold by Shin-Etsu Silicones under the names KSG-21, KSG-20, KSG-30, KSG-31, KSG-32, KSG-33; KSG-210 (dimethicone/PEG-10/15 crosspolymer dispersed in dimethicone); KSG-310 (PEG-15 lauryl dimethicone crosspolymer); KSG-320 (PEG-15 lauryl dimethicone crosspolymer dispersed in isododecane); KSG-330 (PEG-15 lauryl dimethicone crosspolymer dispersed in triethylhexanoin), KSG-340 (PEG-10 lauryl dimethicone crosspolymer and PEG-15 lauryl dimethicone crosspolymer). Other silicone emulsifying elastomers are supplied by Dow Corning™, including PEG-12 dimethicone crosspolymers (DC 9010 and 9011). Other suitable silicone emulsifiers sold by Dow Corning include DC9010 and DC9011. Polyglycerolated emulsifying silicone elastomers are disclosed in PCT/WO 2004/024798. Such elastomers include Shin-Etsu's KSG series, such as KSG-710 (dimethicone/polyglycerin-3 crosspolymer dispersed in dimethicone); or lauryl dimethicone/polyglycerin-3 crosspolymer dispersed in a variety of solvent such as isododecane, dimethicone, triethylhexanoin, available as KSG-810, KSG-820, KSG-830, or KSG-840 from Shin-Etsu.

Structuring agents may be used to increase viscosity, thicken, solidify, or provide solid or crystalline structure to the personal care composition. Structuring agents are typically grouped based on solubility, dispersibility, or phase compatibility. Examples of aqueous or water structuring agents include polymeric agents, natural or synthetic gums, polysaccharides, and the like. In one embodiment, the composition may comprises from about 0.0001%, 0.001%, 0.01%, 0.05%, 0.1%, 0.5%, 1%, 2%, 3%, 5% to about 25%, 20%, 10%, 7%, 5%, 4%, or 2%, by weight of the composition, of one or more structuring agents.

Polysaccharides and gums may be suitable aqueous phase thickening agents. Suitable classes of polymeric structuring agents include but are not limited to carboxylic acid polymers, polyacrylamide polymers, sulfonated polymers, high molecular weight polyalkylglycols or polyglycerins, copolymers thereof, hydrophobically modified derivatives thereof, and mixtures thereof.

Examples of oil structuring agents include silicone and organic based materials. Suitable ranges of oil structuring agents are from about 0.01%, 0.05%, 0.1% 0.5%, 1%, 2.5%, 5%, or 10% to about 30%, 25%, 20%, 15%, 10%, or 5%. Suitable oil phase structuring agents may be silicone based, such as silicone elastomers, silicone gums, silicone waxes, linear silicones having a degree of polymerization allowing the silicone to increase the viscosity of the oil phase. Examples of silicone structuring agents include, but are not limited to, silicone elastomers, silicone gums, and silicone waxes, Suitable silicone elastomers may be in the powder form, or dispersed or solubilized in solvents such as volatile or nonvolatile silicones, or silicone compatible vehicles such as paraffinic hydrocarbons or esters. Examples of silicone elastomer powders include vinyl dimethicone/methicone silsesquioxane crosspolymers like KSP-100, KSP-101, KSP-102, KSP-103, KSP-104, KSP-105, available from Shin-Etsu, hybrid silicone powders that contain a fluoroalkyl group like KSP-200, available from Shin-Etsu, which is a fluoro-silicone elastomer, and hybrid silicone powders that contain a phenyl group such as KSP-300, available from Shin-Etsu, which is a phenyl substituted silicone elastomer; and DC 9506 available from Dow Corning.

Examples of silicone elastomer dispersions include dimethicone/vinyl dimethicone crosspolymers supplied by a variety of suppliers including Dow Corning Corporation under the tradenames DC9040 or DC9041, Momentive under the tradename SFE 839, or Shin-Etsu Silicones under the tradenames KSG-15, 16, 18. KSG-15 has the INCI name cyclopentasiloxane (and) dimethicone/vinyl dimethicone crosspolymer. KSG-18 has the INCI name diphenylsiloxy phenyl trimethicone (and) dimethicone/phenyl vinyl dimethicone crossoplymer. Silicone elastomers may also be purchased from Grant Industries under the Gransil trademark. Other suitable silicone elastomers have long chain alkyl substitutions such as lauryl dimethicone/vinyl dimethicone crosspolymers supplied by Shin Etsu under the tradenames KSG-41, KSG-42, KSG-43, and KSG-44, wherein the elastomer is dispersed in solvents including mineral oil, isodocane, triethylhexanoin, or squalene, respectively. Other suitable silicone elastomers may have polyglycerine substitutions such as lauryl dimethicone/polyglycerin-3 crosspolymers supplied by Shin Etsu under the tradenames KSG-810, KSG-820, KSG-830, and KSG-840, wherein the elastomer is dispersed in solvents including mineral oil, isodocane, triethylhexanoin, or squalene, respectively. Other suitable silicone elastomers may have polyglycol substitutions such as PEG-15/lauryl dimethiconecrosspolymers supplied by Shin Etsu under the tradenames KSG-310, KSG-320, KSG-330, and KSG-340, wherein the elastomer is dispersed in solvents including mineral oil, isodocane, triethylhexanoin, or squalene, respectively. Other suitable silicone elastomers having polyglycol substitutions include Shin Etsu's KSG-210, a dimethicone/PEG-10/15 crosspolymer in dimethicone.

Silicone gums are another oil phase structuring agent. The silicone gum typically has a viscosity ranging from about 500,000 to 100 million cst at 25° C., from about 600,000 to 20 million, from about 600,000 to 12 million cst. Suitable silicone gums include those sold by Wacker-Belsil under the trade names CM3092, Wacker-Belsil 1000, or Wacker-Belsil DM 3096. A particularly suitable silicone gum is as dimethiconol, available from Dow Corning Corporation under the trade name 1-1254 Fluid, 2-9023 Fluid, and 2-9026 Fluid. Dimethiconol is often sold as a mixture with a volatile or nonvolatile silicone such as Dow Corning 1401 Fluid, 1403 Fluid, and 1501 Fluid.

Another type of oily phase structuring agent includes silicone waxes. Silicone waxes may be referred to as alkyl silicone waxes which and are semi-solids or solids at ambient conditions. The term "alkyl silicone wax" means a polydimethylsiloxane having a substituted long chain alkyl (such as C16 to 30) that confers a semi-solid or solid property to the siloxane. Examples of such silicone waxes include stearyl dimethicone, which may be purchased from Evonik Goldschmidt GmbH under the tradename Abil Wax 9800 or from Dow Corning under the tradename 2503. Another example is bis-stearyl dimethicone (which may be purchased from Gransil Industries under the tradename Gransil A-18), behenyl dimethicone, or behenoxy dimethicone.

Other suitable viscosity increasing agents include polyamides and polysilicone-polyamide copolymers. Suitable polysilicone-polyamide copolymers are disclosed in U.S. Patent Application Publication No. 2004/0170586.

Other oil phase structuring agent may be one or more natural or synthetic waxes such as animal, vegetable, or mineral waxes. Suitable silicone waxes are disclosed in U.S. Pat. Nos. 5,413,781 and 5,725,845, and further include alkylmethyl polysiloxanes, C10-C60 alkyl dimethicones, and mixtures thereof.

Other structuring agents include natural or synthetic montmorillonite minerals, silicas, silicates, silica silylate, and alkali metal or alkaline earth metal derivatives thereof.

Optional Ingredients

The personal care composition may comprise one or more optional ingredients.

A. UV Active—The personal care composition may comprise a UV active. UV Actives may be broadly classified as (i) solid UV actives soluble in the isosorbide diester and (ii) other UV Actives.

Suitable solid UV actives soluble in the isosorbide diester include dibenzoylmethane derivatives such as 4-tert-butyl-4'-methoxy dibenzoylmethane (i.e., butyl methoxydibenzoylmethane or avobenzone)(commercially available as PARSOL® 1789 from DSM). Other suitable solid UV actives soluble in the isosorbide diester include bis-ethylhexyloxyphenol methoxyphenyl triazine (i.e., bemotrizinol, commercially available as Tinosorb® S from BASF), 2,4,6-trianilino-(p-carbo-2'-ethylhexyl-1'-oxy)-1,3,5-triazine (i.e., ethylhexyl triazone commercially available as Uvinul® T 150 from BASF), diethylhexyl butamido triazone (i.e., Iscotrizinol, commercially available as Uvasorb® HEB by 3V Sigma), diethylamino hydroxybenzoyl hexyl benzoate (commercially available as Uvinul® A Plus from BASF), benzophenone-3 (i.e., (2-Hydroxy-4-methoxyphenyl)-phenylmethanone or oxybenzone, available Eusolex 4360 from EMD Chemical, Inc.), 4-methylbenzylidene camphor (commercially available as PARSOL® 5000 from DSM), ethylhexyl bis-isopentylbenzoxazolylphenyl melamine (commercially available as Uvasorb® k2A by 3V Sigma), and combinations thereof.

In certain embodiments, the solid UV active soluble in the isosorbide diester is selected from 4-tert-butyl-4'-methoxy dibenzoylmethane, bis-ethylhexyloxyphenol methoxyphenyl triazine, and combinations thereof.

The personal care composition may comprise an amount of the solid UV active soluble in the isosorbide diester to provide a desired UV absorption or sunscreen benefit. The personal care composition may comprise an amount of the solid UV active soluble in the isosorbide diester as prescribed or proposed by regulatory agencies in the US (e.g., 21 CFR part 352, 68 Federal Register 41386, 70 Federal Register 72449, or 71 Federal Register 42405), Europe (Regulation No 1223/2009 of the EU Parliament; Annex VI), Japan, China, Australia, New Zealand, or Canada. In particular embodiments, the personal care composition comprises from about 0.01% to about 20%, by weight of the composition, of a solid UV active soluble in the isosorbide diester. In other embodiments, the personal care composition comprises from about 0.1%, 0.5%, or 1% to about 15%, 10%, 6%, 5%, or 3%, by weight of the composition, of a solid UV active soluble in the isosorbide diester. In another embodiment, the personal care composition may comprise a sufficient about of solid UV active to yield a Sun Protection Factor of at least about 15, 30 45, or 50. SPF testing is conventional and well understood in the art. A suitable SPF test is prescribed in 21 C.F.R. 352, Subpart D. In other embodiments, the personal care composition may comprise a sufficient about of solid UV active soluble in the isosorbide diester to yield a UVA protection value of low, medium, high, or, ideally, highest, as defined by the U.S. Federal Drug Administration in sections 352.71-73 in the proposed rule published in 72 Federal Register 49070 on Aug. 27, 2007.

"Other UV Active" means UV actives that are not solid or are not soluble in the isosorbide diester as described above. The personal care composition may comprise an amount of additional UV active to provide a desired UV absorption or sunscreen benefit. The composition may comprise from about 0.0001%, 0.001%, 0.01%, 0.05%, 0.1%, 0.5%, or 1% to about 20%, 10%, 7%, or 5%, by weight of the composition, of a suitable Other UV Active. In another embodiment, the personal care composition may comprise a sufficient about of additional UV active to yield a Sun Protection Factor of at least about 15, 30 45, or 50. In other embodiments, the personal care composition may comprise a sufficient about of the Other UV Active to yield a UVA protection value of low, medium, high, or, ideally, highest.

Suitable Other UV Actives include dibenzoylmethane compounds other than 4-tert-butyl-4'-methoxy dibenzoylmethane. Other suitable additional UV actives include 2-ethylhexyl-p-methoxycinnamate; octyldimethyl-p-aminobenzoic acid; 2-ethylhexyl-2-cyano-3,3-diphenylacrylate; 2-ethylhexyl salicylate; 2-phenylbenzimidazole-5-sulfonic acid; 2-(p-dimethylaminophenyl)-5-sulfonicbenzoxazoic acid; disodium phenyl dibenzimidazole tetrasulfonate; sodium dihydroxy dimethoxy disulfobenzophenone; polysilicone-15; isoamyl p-methoxycinnamate; and combinations thereof. Suitable Other UV Actives include inorganic particulates such as zinc oxide and titanium dioxide and organic particulates such as methylene bis-benzotriazolyl tetramethylbutylphenol (commercially available as Tinosorb® M from BASF).

In a select embodiment, the personal care composition comprises at least 1 part, by weight, of 2-ethylhexyl-2-cyano-3,3-diphenylacrylate to every 1 part, by weight, of the solid UV active, wherein the solid UV active is 4-tert-butyl-4'-methoxy dibenzoylmethane.

B. Photostabilizers—The personal care composition may comprise a photostabilizer. The composition may comprise from about 0.0001%, 0.001%, 0.01%, 0.05%, 0.1%, 0.5%, or 1% to about 20%, 10%, 7%, or 5%, by weight of the composition, of one or more suitable photostabilizer.

A suitable photostabilizer is alpha-cyanodiphenylacrylate is as disclosed in U.S. Pat. No. 7,713,519. The alpha-cyanodiphenylacrylate may have the general formula:

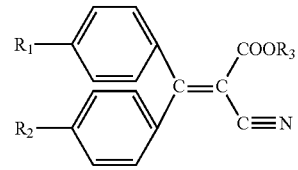

wherein one or both of R1 and R2 is independently a straight or branched chain C1-30 alkoxy radical and any non-alkoxy R1 or R2 radical is hydrogen; and R3 is a straight or branched chain C1-30 alkyl. Alternately, one or both of R1 and R2 is independently a C1-8 alkoxy radical and any non-alkoxy R1 or R2 radical is hydrogen; and R3 is a straight of branched chain C2-20 alkyl. Alternately, one or both of R1 and R2 is independently methoxy, and any non-methoxy R1 or R2 is hydrogen; and R3 is a straight or branched chain C2-20 alkyl.

A suitable alpha-cyanodiphenylacrylate is ethylhexyl methoxycrylene, or 2-ethylhexyl 2-cyano-3-(4-methoxyphenyl)-3-phenylpropenoate, wherein R1 is methoxy, R2 is hydrogen, and R3 is 2-ethylhexyl. This material is available from Hallstar Company under trade name Solastay® S1.

Another suitable photostabilizer includes diesters or polyesters of naphthalene dicarboxylic acid as disclosed in U.S. Pat. Nos. 5,993,789, 6,113,931, 6,126,925 and 6,284,916. Suitable diesters or polyesters of naphthalene dicarboxylic acid may have the following formula:

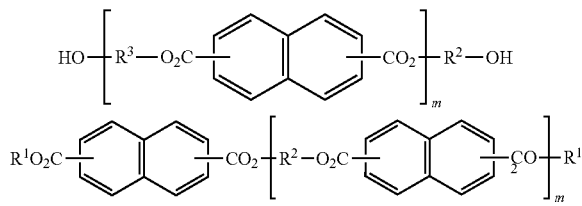

wherein each R¹ independently is an alkyl group having 1 to 22 carbon atoms, or a diol having the formula HO—R²—OH, or a polyglycol having the formula HO—R³—(—O—R²—)$_m$—OH, and, wherein R² and R³, same or different, are each an alkylene group, straight chain or branched, having 1 to 6 carbon atoms, wherein m and n are each 1 to about 100, 1 to about 10, or 2 to about 7. A suitable diester of naphthalene dicarboxylic acid is diethylhexyl 2,6-naphthalate available as Corapan® TQ from Symrise.

Another suitable photostabilizer is 4-hydroxybenzylidenemalonate derivatives or 4-hydroxycinnamate derivatives. Suitable materials may have the following formula:

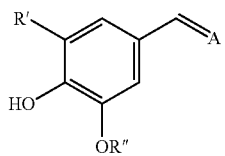

wherein A is a chromophoric group that absorbs UV-radiation, comprises one divalent group or two monovalent groups with at least one group having carbonyl (C=O) functionality; R' is hydrogen, a linear or branched $C_1$-$C_8$ alkyl radical or a linear or branched $C_1$-$C_8$ alkoxy radical; and R" is a linear or branched $C_1$-$C_8$ alkyl radical. Exemplary compounds include ethyl-alpha-cyano-3,5-dimethoxy-4-hydroxy cinnamate, ethyl-alpha-acetyl-3,5-dimethoxy-4-hydroxy cinnamate, iso-propyl-alpha-acetyl-3,5-dimethoxy-4-hydroxy cinnamate, iso-amyl-alpha-acetyl-3,5-dimethoxy-4-hydroxy cinnamate, 2-ethylhexyl-alpha-acetyl-3,5-dimethoxy-4-hydroxy cinnamate, diethyl-3,5-dimethoxy-4-hydroxy benzylidene malonate, di-(2-ethylhexyl)-3,5-dimethoxy-4-hydroxy benzylidene malonate, diisoamyl-3,5-dimethoxy-4-hydroxy benzylidene malonate, didodecyl-3,5-dimethoxy-4-hydroxy benzylidene malonate, dipalmitoyl-3,5-dimethoxy-4-hydroxy benzylidene malonate, and di-isopropyl-3,5-dimethoxy-4-hydroxy benzylidene malonate. A particularly suitable compound is diethylhexyl syringylidenemalonate (INCI name) available under the tradename Oxynex® ST from EMD Chemicals, Inc. Additional suitable 4-hydroxybenzylidenemalonate derivatives or 4-hydroxycinnamate derivatives are disclosed in U.S. Pat. No. 7,357,919 and U.S. Patent Application Publication No. 2003/0108492A1 and US2003/0157035A.

Other suitable photostabilizers include a 2-pyrrolidinone-4-carboxy ester compounds as described in U.S. Patent Application Publication No. 2010/0183529; silicon-containing s-triazines substituted with two aminobenzoate or aminobenzamide groups as described in U.S. Patent Application Publication No. 2008/0145324; fluorene derivatives as described in U.S. Patent Application Publications Nos. 2004/00579912, 2004/00579914, 200/00579916, and 2004/062726; piperidinol salts as described in U.S. Patent Application Publications No. 2005/0220727 including tris(tetramethylhydroxypiperidinol) citrate sold under the tradename Tinogard® Q by Ciba; and arylalkyl amides and esters as described in U.S. Patent Application Publication No. 2008/0019930.

Other suitable photostabilizers are listed in the functional category of "Light Stabilizers" in the Personal Care Product Council's *International Cosmetic Ingredient Dictionary and Handbook*, Thirteenth Edition, 2010.

C. Optional Actives—The personal care compositions may comprise one or more optional components to provide an efficacious and/or consumer desirable product. For example, the composition can include other actives or agents. For instance, suitable optional skin care actives and agents may include an active or agent selected from a group consisting of sugar amines, vitamins, oil control agents, photosterols, hexamidine compounds, hyaluronin (low molecular weight of less than 200 kD, or high molecular weight of greater than 200 kD), hyaluronin sodium salt (low molecular weight of less than 200 kD, or high molecular weight of greater than 200 kD), hyaluronic acid (low molecular weight of less than 200 kD, or high molecular weight of greater than 200 kD), hyaluronic acid sodium salt (low molecular weight of less than 200 kD, or high molecular weight of greater than 200 kD), tightening agents, anti-wrinkle actives, anti-atrophy actives, retinoids, peptides, particulate materials, UV actives, photostabilizers, anti-cellulite agents, desquamation actives, anti-acne actives, anti-oxidants, radical scavengers, conditioning agents, anti-inflammatory agents, tanning actives, skin lightening agents, botanical extracts, antimicrobial actives, antifungal actives, antibacterial actives, antiperspirant actives, preservatives, anti-dandruff actives, detersive surfactants, and combinations thereof. Examples of these materials are provided in U.S. Patent Application Publication No. US2007/0185038A1, US2006/0275237A1, US2004/0175347A1, and US2006/0263309A1. The personal care composition may comprise from about 0.0001%, 0.001%, 0.01%, 0.05%, 0.1%, 0.5%, 1%, 2%, or 3% to about 30%, 25%, 20%, 15%, 10%, 7%, 5%, 3%, 2%, or 1%, by weight of the composition, of one or more skin care actives.

In certain embodiments, skin care actives may be selected from sugar amines, vitamins, hexamidine compounds, peptides, and combinations thereof.

Examples of sugar amines that are useful herein include glucosamine, N-acetyl glucosamine, mannosamine, N-acetyl mannosamine, galactosamine, N-acetyl galactosamine, their isomers (e.g., stereoisomers), and their salts (e.g., HCl salt). Preferred for use herein are glucosamine, particularly D-glucosamine and N-acetyl glucosamine, particularly N-acetyl-D-glucosamine.

"Vitamins" means vitamins, pro-vitamins, and their salts, isomers and derivatives. Non-limiting examples of suitable vitamins include: vitamin B compounds (including B1 compounds, B2 compounds, B3 compound, B5 compounds, such as panthenol or "pro-B5", pantothenic acid, pantothenyl; B6 compounds, such as pyroxidine, pyridoxal, pyridoxamine; carnitine, thiamine, riboflavin); vitamin A compounds, and all natural and/or synthetic analogs of Vitamin A, including retinoids, retinol, retinyl acetate, retinyl palmitate, retinoic acid, retinaldehyde, retinyl propionate, carotenoids (pro-vitamin A), and other compounds which possess the biological activity of Vitamin A; vitamin D compounds; vitamin K compounds; vitamin E compounds, or tocopherol, including tocopherol sorbate, tocopherol acetate, other esters of tocopherol and tocopheryl compounds; vitamin C compounds, including ascorbate, ascorbyl esters of fatty acids, and ascorbic acid derivatives, for example, ascorbyl phosphates such as magnesium ascorbyl phosphate and sodium ascorbyl phosphate, ascorbyl glucoside, and ascorbyl sorbate; and vitamin F compounds, such as saturated and/or unsaturated fatty acids.

In certain embodiments, the personal care compositions comprise a vitamin B3 compound. As used herein, "vitamin B3 compound" means a compound having the formula:

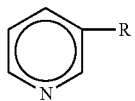

wherein R is —CONH$_2$ (i.e., niacinamide), —COOH (i.e., nicotinic acid) or —CH2OH (i.e., nicotinyl alcohol); derivatives thereof; and salts of any of the foregoing.

The personal care compositions may include hexamidine compounds, its salts, and derivatives. As used herein, "hexamidine compound" means a compound having the formula:

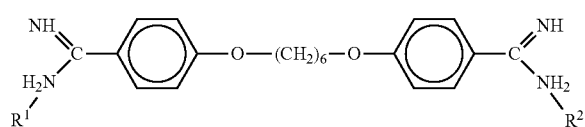

wherein R$^1$ and R$^2$ are optional or are organic acids (e.g., sulfonic acids, etc.) A suitable hexamidine compounds includes hexamidine diisethionate, commercially available as Eleastab® HP100 from Laboratoires Serobiologiques.

As used herein, "peptide" refers to peptides containing ten or fewer amino acids and their derivatives, isomers, and complexes with other species such as metal ions (e.g., copper, zinc, manganese, magnesium, and the like). Peptide refers to both naturally occurring and synthesized peptides. Also useful herein are naturally occurring and commercially available compositions that contain peptides. The peptides may contain at least one basic amino acid (e.g., histidine, lysine, arginine). For example, suitable peptides are the dipeptide carnosine (beta-ala-his), the tripeptide gly-his-lys, the tripeptide his-gly-gly, the tripeptide gly-gly-his, the tripeptide gly-his-gly, the tetrapeptide gly-gln-pro-arg, the pentapeptide lys-thr-thr-lys-ser, lipophilic derivatives of peptides, and metal complexes of the aforementioned (e.g., copper complex of the tripeptide his-gly-gly (also known as Iamin)) Other suitable peptides include Peptide CK (arg-lys-arg); Peptide CK+ (ac-arg-lys-arg-NH2); and Peptide E, arg-ser-arg-lys. A commercially available tripeptide derivative-containing composition is Biopeptide CL® (from Sederma, France), which contains 100 ppm of palmitoyl-gly-his-lys and is commercially available. A commercially available pentapeptide derivative-containing composition is Matrixyl® (from Sederma, France), which contains 100 ppm of palmitoyl-lys-thr-thr-lys-ser. A suitable peptide is a dipeptide based molecule having a C terminal amino acid of threonine, such as plamitoyl-lys-thr, as described in US Patent Application Publication 2007/0020220 A1.

Peptide derivatives useful herein include lipophilic derivatives such as palmitoyl derivatives. In one embodiment, the peptide is selected from palmitoyl-lys-thr-thr-lys-ser, palmitoyl-gly-his-lys, their derivatives, and combinations thereof.

The particular sensory agents herein, can be blended in a suitable carrier as described at a concentration ranging from about 0.0001% to about 10.0%, preferably from about 0.001% to about 2.0%, more preferably from about 0.01% to about 1.0%, by weight of the formula composition. The sensory agent can also be prepared in a premix in an oil diluent. Nonetheless, the final concentration of the active principal will fall in the range described above.

Other suitable optional components can also be included in the personal care composition of the present invention, such as those included, but not limited to, the following functional classes: abrasives, absorbents, fragrances, anti-acne agents, anti-caking agents, antifoaming agents, antimicrobial agents (e.g., iodopropyl butylcarbamate), antifungal agents, antioxidants, binders, buffering agents, bulking agents, chelating agents, colorants, cosmetic astringents, cosmetic biocides, denaturants, drug astringents, external analgesics, film formers, opacifying agents, pH adjusters, plant derivatives, plant extracts, plant tissue extracts, plant seed extracts, plant oils, botanicals, botanical extracts, preservatives, propellants, reducing agents, sebum control agents, sequestrants, skin bleaching agents, skin-conditioning agents (e.g. humectants and occlusive agents), and skin protectorants. Other suitable optional person care ingredients include materials listed in paragraphs 513-839 of U.S Patent Application No. 2010/0112100.

Methods of Using the Personal Care Compositions

The personal care compositions of the present invention are useful for improving or regulating a number of keratinous tissue conditions. As used in relation to methods of using the personal care compositions, "regulating" means maintaining skin appearance and/or feel of the keratinous tissue with little to no degradation in appearance and/or feel, and "improving" means affecting a positive change in keratinous tissue appearance and/or feel. The keratinous tissue appearance and/or feel benefit may be an acute or chronic benefit. In other embodiments, the personal care composition may result in a physiological change of the keratinous tissue.

Keratinous tissue conditions that may be regulated or improved include, but are not limited to thickening keratinous tissue (e.g., building the epidermis and/or dermis and/or subcutaneous layers of the skin and where applicable the keratinous layers of the nail and hair shaft), atrophy, softening and/or smoothing, itch, appearance of dark undereye circles and/or puffy eyes, sallowness, sagging (e.g., glycation), tanning, desquamating, exfoliating, and/or increasing turnover in mammalian skin, pores size, oily/shiny appearance, hyperpigmentation such as post-inflammatory hyperpigmentation, spider vessels and/or red blotchiness on mammalian skin, fine lines and wrinkles, dryness (e.g., roughness, scaling, flaking), cellulite, and acne.

Other keratinous conditions that may be regulated or improved include signs of skin aging including, but not limited to, all outward visibly and tactilely perceptible manifestations, as well as any macro- or micro-effects, due to keratinous tissue aging. These signs may result from processes which include, but are not limited to, the development of textural discontinuities such as wrinkles and coarse deep wrinkles, fine lines, skin lines, crevices, bumps, large pores, unevenness or roughness; loss of skin elasticity; discoloration (including undereye circles); blotchiness; sallowness; hyperpigmented skin regions such as age spots and freckles; keratoses; abnormal differentiation; hyperkeratinization; elastosis; collagen breakdown, and other histological changes in the stratum corneum, dermis, epidermis, vascular system (e.g., telangiectasia or spider vessels), and underlying tissues (e.g., fat and/or muscle), especially those proximate to the skin.

The personal care compositions of the present invention are useful for improving or regulating insult-affected keratinous tissue. "Insult-affected keratinous tissue," means keratinous tissue which exhibits discomfort, irritation, an unpleasant or irregular appearance, and the like, for example after exposure to a physical and/or chemical irritant. Non-limiting examples of insult-affected keratinous tissue include burn (e.g., sunburns, windburn, chemical or thermal burns); rashes (e.g., diaper rash, shaving rash and allergen-induced rashes); discoloration (e.g., bleaching, staining, hyperpigmentation); nicks and cuts (e.g., shaving insults); and dry, chapped or rough skin (e.g., due to exposure to example wind, cold and/or low humidity). Non-limiting examples of insults include radiation, wind, low humidity, allergens, pollutants, chemical and natural irritants, bodily fluids, bodily waste, excessive moisture, bacteria, fungi, etc.

Method of Making the Personal Care Compositions

As presented above, the personal care composition may take a variety of forms. The following methods are exemplary and are not to be read as limiting. When the personal care composition is in the form of an oil dispersion or solution, the following method may be used. A sufficient amount of isosorbide diester is provided to solubilize the solid cosmetic active. In a suitable vessel, the solid cosmetic active is combined with the isosorbide diester. The combination may be mixed (e.g., magnetic stirrer with spin bar) and optionally heated to 70° C. Additional materials soluble and/or compatible may also be added. The composition is mixed until no solute is visible. Mixing or homogenization may be done by devices and techniques known in the art. Suitable methods and devices include mechanical techniques such as mixers or shaker plate, high pressure techniques such as sonolators or liquid whistles, and ultrasonic techniques such as sonicators. Typically mixing and the optional heating at 70° C. are performed for no more than 10 minutes. The composition may be transferred to an acceptable container. The composition may be cooled.

When the personal care composition is in the form of an emulsion, the oil phase may be prepared according to the method above. A separate vessel the aqueous phase is prepared by combining the aqueous carrier such as water and/or a water miscible solvent with any water soluble materials, if present. The combination may be mixed (e.g., magnetic stirrer with spin bar) and optionally heated to 70° C. Depending upon the particular emulsion form (O/W or W/O) an emulsifier may be added to the suitable phase. Typically, the emulsifier may be added to the continuous phase. Again, depending upon the desired emulsion form, the oil phase may be added to the aqueous phase or vice versa. The emulsion may be mixed (e.g., magnetic stirrer with spin bar) and optionally heated to 70° C. The composition is mixed until no solute is visible. Mixing or homogenization may be done by devices and techniques known in the art. Typically mixing and the optional heating at 70° C. are performed for no more than 10 minutes. The emulsion may be transferred to an acceptable container. The emulsion may be cooled.

Examples 1-6 are personal care compositions comprising a solid cosmetic active soluble in the isosorbide diester.

|  | 1 | 2 | 3 | 4 | 5 | 6 |
|---|---|---|---|---|---|---|
| Water Phase: | | | | | | |
| Water | qs | qs | qs | qs | qs | qs |
| Glycerin | 5.0 | 5.0 | 5.0 | 5.0 | 5.0 | 5.0 |
| Disodium EDTA | 0.1 | 0.1 | 0.1 | 0.1 | 0.1 | 0.1 |
| Methylparaben | 0.2 | 0.2 | 0.2 | 0.2 | 0.2 | 0.2 |
| Niacinamide | 4.0 | 4.0 | 4.0 | 4.0 | 4.0 | 4.0 |
| D-panthenol | 0.5 | 0.5 | 0.5 | 0.5 | 0.5 | 0.5 |
| Pentylene Glycol | 1.0 | 1.0 | 1.0 | 1.0 | 1.0 | 1.0 |
| Benzyl alcohol | 0.25 | 0.25 | 0.25 | 0.25 | 0.25 | 0.25 |
| Triethanolamine | 0.64 | 0.64 | 0.64 | 0.64 | 0.64 | 0.64 |
| Oil Phase: | | | | | | |
| Isopropyl Isostearate | 1.33 | 1.33 | 1.33 | 1.33 | 1.33 | 1.33 |
| Octisalate | — | — | — | 4.0 | 4.0 | — |
| Octocrylene | — | — | — | 1.0 | 1.0 | — |
| Avobenzone | — | — | — | 2.0 | 1.0 | — |
| Vitamin E Acetate | 0.1 | 0.1 | 0.1 | 0.1 | 0.1 | 0.1 |
| Ethylparaben | 0.2 | 0.2 | 0.2 | 0.2 | 0.2 | 0.2 |
| Propylparaben | 0.2 | 0.2 | 0.2 | 0.2 | 0.2 | 0.2 |
| Cetyl alcohol | 0.3 | 0.3 | 0.3 | 0.3 | 0.3 | 0.3 |
| Stearyl alcohol | 0.4 | 0.4 | 0.4 | 0.4 | 0.4 | 0.4 |
| Behenyl alcohol | 0.4 | 0.4 | 0.4 | 0.4 | 0.4 | 0.4 |
| Cetearyl Glucoside/Cetearyl Alcohol[1] | 0.3 | 0.3 | 0.3 | 0.3 | 0.3 | 0.3 |
| PEG-100 stearate | 0.3 | 0.3 | 0.3 | 0.3 | 0.3 | 0.3 |
| Tinosorb S[5] | — | — | — | — | 1.0 | — |
| Synovea DOI[6] | 4.0 | 5.0 | 6.0 | 6.0 | 8.0 | 9.0 |
| (S)-Equol[7] | — | — | 0.35 | — | — | — |
| Tetrahydrocurcuminoids[8] | — | 0.15 | — | — | — | 0.10 |
| Hexylresorcinol[9] | 2.0 | — | — | 2.0 | 1.0 | 1.0 |
| Thickener: | | | | | | |
| Sepigel ™ 305[2] | 2.25 | 2.25 | 2.25 | 2.25 | 2.25 | 2.25 |
| Additional Ingredients: | | | | | | |
| Microthene FN510[3] | 1.0 | 1.0 | 1.0 | 1.0 | 1.0 | 1.0 |
| Polysorbate 20 | 0.5 | 0.5 | 0.5 | 0.5 | 0.5 | 0.5 |
| Dow Corning ™ 1503[4] | 2.0 | 2.0 | 2.0 | 2.0 | 2.0 | 2.0 |
| Total: | 100% | 100% | 100% | 100% | 100% | 100% |

[1]Emulgade ™ PL68/50 from Cognis ™
[2]Polyacrylamide, C13-14 isoparaffin, and laureth-7 from Seppic ™
[3]Polyethylene homopolymer spheres from Equistar ™
[4]Dimethicone and dimethiconol from Dow Corning ™
[5]Bis-Ethylhexyloxyphenol Methoxyphenyl Triazine from BASF ™
[6]Dioctanoyl Isosorbide from Syntheon, Ltd., Boonton, NJ.
[7]Available from Girindus America, Inc., Reading, OH.
[8]Available from Sabinsa Corporation, East Windsor, NJ.
[9]Synovea ® HR available from Sytheon, Ltd., Lincoln Park, NJ.

In a suitable vessel, the water phase ingredients are combined and heated to 75° C. In a separate suitable vessel, the oil phase ingredients are combined and heated to 75° C. Next the oil phase is added to the water phase and the resulting emulsion is milled (e.g., with a Tekmar T-25). The thickener is then added to the emulsion and the emulsion is cooled to 45° C. while stirring. At 45° C., the remaining additional ingredients are added. The product is then cooled with stirring to 30° C., milled again, and then poured into suitable containers.

TEST EXAMPLES

In the testing provided below, "soluble" (or "solubilize"), in relation to the solubility of a solid solute being tested, means that no visible crystals may be seen after a prescribed storage period at a storage condition. The storage period can vary. Suitable storage periods include about 24 hours, about 1 week, and about 30 days. Suitable storage conditions include ambient conditions or cold storage at 5° C. (approximately 1 atm). In certain embodiments, solubility may be determined after a 24 hour storage period at ambient conditions. In other embodiments, solubility may be determined after 20 days in cold storage. Other testing parameters may include storage for prolonged time periods (e.g., 30 day, 50 days, 60 days, 90 days) and at variable temperatures (e.g., 5° C., 50° C.).

Example 1

The solvency of an isosorbide diester within the scope of the present invention was tested against two conventional, industry standard solvents. The solvency of isosorbide dicaprylate, isopropyl lauroyl sarcosinate, and $C_{12}$-15 alkyl benzoate was tested using (S)-Equol (i.e., 4',7-isoflavandiol, commercially available from Girindus America, Inc, Reading, Ohio) as the solid cosmetic active. A test solution was of 6% Equol is prepared with heating to 70° C. Upon reaching 70° C., the examples may be mixed for about 10 minutes. Place mixtures in a covered vial and cool to the storage temperature. Solubility is evaluated for samples stored 24 hours at ambient conditions. Solubility is also evaluated for samples stored for 7 day at 5° C. followed by equilibration to ambient conditions. Results are shown in Table 1. The data demonstrates that the solvency of the isosorbide diester is equivalent or superior to the industry leading solvents.

TABLE 1

| Approximately 1:16 solute to solvent ratio | Solute:Solvent Ratio | |
| --- | --- | --- |
| | 24 hour rest at Ambient Conditions | 7 day storage at 5° C. |
| 1A. Isosorbide dicaprylate | Soluble | Soluble |
| 1B. Isopropyl lauroyl sarcosinate* | Soluble | Soluble |
| 1C. C12-15 alkyl benzoate* | Insoluble | Insoluble |

*Comparative Examples

Example 2

The solvency of an isosorbide diester within the scope of the present invention was tested against two conventional, industry standard solvents. The solvency of isosorbide dicaprylate, isopropyl lauroyl sarcosinate, and C12-15 alkyl benzoate was tested when using tetrahydrocurcuminoids (THC) (commercially available as tetrahydrocurcuminoids from Sabinsa Corporation, East Windsor, N.J.) as the solid cosmetic active. A test solution of 3% THC is prepared with heating to 70° C. Upon reaching 70° C., the examples may be mixed for about 10 minutes. Place mixtures in a covered vial and cool to the storage temperature. Solubility is evaluated for samples stored 24 hours at ambient conditions. Solubility is also evaluated for samples stored for 7 day at 5° C. followed by equilibration to ambient conditions. Results are shown in Table 2. The data demonstrates that the solvency of the isosorbide diester is equivalent or superior to the industry leading solvents.

TABLE 2

| Approximately 1:32 solute to solvent ratio | Solute:Solvent Ratio | |
| --- | --- | --- |
| | 24 hour rest at Ambient Conditions | 7 day storage at 5° C. |
| 1A. Isosorbide dicaprylate | Soluble | Soluble |
| 1B. Isopropyl lauroyl sarcosinate* | Soluble | Soluble |
| 1C. C12-15 alkyl benzoate* | Insoluble | Insoluble |

*Comparative Examples

Example 3

The solvency of an isosorbide diester within the scope of the present invention was tested against two conventional, industry standard solvents. The solvency of isosorbide dicaprylate, isopropyl lauroyl sarcosinate, and C12-15 alkyl benzoate was tested when using hexylresorcinol (commercially available as Synovea® HR from Sytheon, Ltd.) as the solid cosmetic active. A test solution of 33.5% hexylresorcinol is prepared with heating to 70° C. Upon reaching 70° C., the examples may be mixed for about 10 minutes. Place mixtures in a covered vial and cool to the storage temperature. Solubility is evaluated for samples stored 24 hours at ambient conditions. Solubility is also evaluated for samples stored for 7 day at 5° C. followed by equilibration to ambient conditions. Results are shown in Table 3. The data demonstrates that the solvency of the isosorbide diester is equivalent or superior to the industry leading solvents.

TABLE 3

| Approximately 1:2 solute to solvent ratio | Solute:Solvent Ratio | |
| --- | --- | --- |
| | 24 hour rest at Ambient Conditions | 7 day storage at 5° C. |
| 1A. Isosorbide dicaprylate | Soluble | Soluble |
| 1B. Isopropyl lauroyl sarcosinate* | Soluble | Soluble |
| 1C. C12-15 alkyl benzoate* | Soluble | Soluble |

*Comparative Examples

Feminine Intimate Moisturizer or Lubricant

| | 1 | 2 | 3 | 4 | 5 | 6 | 7 |
| --- | --- | --- | --- | --- | --- | --- | --- |
| Water Phase: | | | | | | | |
| Water | qs | qs | qs | qs | qs | qs | qs |
| Glycerin | 3.0 | 5.0 | — | 1.0 | 1.0 | 3.0 | 3.0 |
| Disodium EDTA | 0.1 | 0.1 | 0.1 | 0.1 | 0.1 | 0.1 | 0.1 |
| Niacinamide | 0.5 | 2.0 | 4.0 | 1.0 | 3.0 | 2.0 | 2.0 |
| D-panthenol | 0.5 | 0.5 | 0.5 | 0.5 | 0.5 | 0.5 | 0.5 |
| Pentylene Glycol | 1.0 | 1.0 | 1.0 | 1.0 | 1.0 | 1.0 | 1.0 |
| Hyaluronin sodium salt, High molecular weight[10] | 1.0 | — | 0.2 | — | — | — | — |
| ... Hyaluronin, low molecular weight[10] | — | 0.5 | — | — | 0.1 | — | — |
| Oil Phase: | | | | | | | |
| Isopropyl Isostearate | 4.0 | 1.33 | | | 1.0 | 1.5 | 1.5 |
| Isopropyl lauroyl sarcosinate[11] | — | — | 4.0 | 4.0 | 3.0 | 1.0 | — |

-continued

|  | 1 | 2 | 3 | 4 | 5 | 6 | 7 |
|---|---|---|---|---|---|---|---|
| Vitamin E Acetate | 0.1 | 0.1 | 0.1 | 0.1 | 0.1 | 0.1 | 0.1 |
| Ethylparaben | 0.2 | 0.2 | 0.2 | 0.2 | 0.2 | 0.2 | 0.2 |
| Propylparaben | 0.1 | 0.1 | 0.1 | 0.1 | 0.1 | 0.1 | 0.1 |
| CF-600 Polymethylsilsesquioxane[12] | 0.25 | — | 0.25 | — | 0.25 | — | — |
| Myrj 59[13] | — | — | 0.1 | — | 0.1 | 0.3 | 0.1 |
| Cetyl alcohol | 0.3 | 0.3 | 0.3 | 0.3 | 0.3 | 0.3 | 0.3 |
| Stearyl alcohol | 0.5 | 0.5 | 0.5 | 0.5 | 0.5 | 0.5 | 0.5 |
| Behenyl alcohol | 0.4 | 0.4 | 0.4 | 0.4 | 0.4 | 0.4 | 0.4 |
| Cetearyl Glucoside/ Cetearyl Alcohol | 0.3 | 0.3 | 0.3 | 0.3 | 0.3 | 0.3 | 0.3 |
| (S)-Equol[7] | 1.0 | 0.2 | 1.0 | 0.5 | 1.0 | 0.5 | 0.1 |
| Lipex Omega Passiflora[14] | 3.0 | 1.0 | 5.0 | 0.1 | 0.5 | — | — |
| Lipex Omega 3/6[14] | 0.1 | 2.0 | — | 4.0 | 2.0 | 0.5 | — |
| Dow Corning Xiameter PMX-200 100 cs[15] | 0.5 |  |  | 0.2 | 0.3 |  | — |
| Dow Corning Xiameter PMX-200 350 cs[15] |  | 0.5 |  | 0.2 |  |  | — |
| Dow Corning Xiameter PMX-0245 (n = 6)[15] | — | — | 0.5 | — | 0.2 | — | — |
| Frescolat MGA[16] |  |  |  |  |  |  | 0.1 |
| Thickener: |  |  |  |  |  |  |  |
| Sepigel ™ 305 | 2.25 | 2.25 | 2.25 | 2.25 | 2.25 | 2.25 | 2.25 |
| Additional Ingredients: |  |  |  |  |  |  |  |
| Benzyl alcohol | 0.25 | 0.25 | 0.25 | 0.25 | 0.25 | 0.25 | 0.25 |
| Dow Corning 1503 | 2.0 | 2.0 | 2.0 | 2.0 | 2.0 | 2.0 | 2.0 |
| Total: | 100% | 100% | 100% | 100% |  | 100% | 100% |

[10]from Soliance
[11]Eldew SL-205 from Ajinomoto
[12]from Momentive
[13]from Croda
[14]from Aarhus Karlshamn Sweden AB
[15]from Dow Corning Corporation
[16]from Symrise In a suitable vessel, the water phase ingredients are combined and heated to 70-80° C. and mixed with Tekmar mixer equipped with a propeller blade. In a separate suitable vessel, the oil phase ingredients are combined and heated to 70-80° C. and mixed. When the oil and water phases are stable at 75° C., the oil phase is added to the water phase and the resulting emulsion is milled (e.g., with a Tekmar T-25). The thickener is then added to the emulsion at approximately 60° C., and the emulsion is cooled to 45° C. while stirring. At 45° C., the remaining additional ingredients are added. The product is then cooled with stirring to 30° C., milled again, and then poured into suitable containers.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of regulating dryness in urogenital skin comprising applying a composition to one or more tissues of a female body experiencing dryness, wherein the tissue is the introitus, wherein the composition comprises:
   a. from about 0.1% to about 3% of a Vitamin B5 compound selected from the group consisting of panthenol, pantothenic acid, pantothenyl and mixtures thereof,
   b. from about 0.1% to about 7% of a Vitamin B3 compound selected form the group consisting of niacinamide, nicotinic acid, nicotinyl alcohol, salts thereof and mixtures thereof,
   c. from about 0.01 to 2% of a Vitamin E compound selected from the group consisting of tocopherol, tocopherol succinate, tocopherol sorbate, tocopherol acetate and mixtures thereof;
   d. from about 0.01% to about 10% of an active selected from the group consisting of hyaluronin, hyaluronin sodium salt, hyaluronic acid, hyaluronic acid sodium salt, and mixtures thereof;
   e. from about 0.1% to about 30% of a silicone oil;
   f. less than 0.01% of a polysaccharide thickening agent; and
   g. a polyacrylamide polymer.

2. The method of claim 1 wherein the composition comprises from about 50% to about 95% water.

3. The method of claim 1 wherein the composition is an oil-in-water emulsion.

4. The method of claim 1 wherein the composition further comprises from about 1% to about 25% a water miscible solvent selected from the group consisting of dihydric alcohols, polyhydric alcohols, glycerol, glycols, polyalkylene glycols, and mixtures thereof.

5. The method of claim 4 wherein the water miscible solvent is selected from the group consisting of glycerol, polyethylene glycol, 1,2-propanediol, 1,3- propanediol, butanediol, pentanediol, hexanediol, heptanediol, decanediol, and mixtures thereof.

6. The method of claim 5 wherein the water miscible solvent is glycerol.

7. The method of claim 1 wherein the composition is substantially free of cleansing or detersive surfactants.

8. The method of claim 1, wherein the silicone oil is selected from the group consisting of a polysiloxane, dimethicone, dimethiconol, cyclic silicones and mixtures thereof.

9. The method of claim 8, wherein said silicone oil is polysiloxane.

10. The method of claim 9, wherein said polysiloxane has the following structure:

$$R_3SiO[R_2SiO]_xSiR_3$$

wherein R is independently selected from hydrogen or a $C_{1-30}$ straight or branched chain, saturated or unsaturated alkyl, phenyl or aryl, trialkylsiloxy; and x is an integer from 0 to about 10,000.

11. The method of claim 10, wherein R is hydrogen, methyl or ethyl.

12. The method of claim 8, where said wherein said silicone oil is dimethicone.

13. The method of claim 12, wherein said dimethicone has the following structure:

$$R_3SiO[R_2SiO]_x[RR'SiO]_ySiR_3$$

wherein R and R' are each independently selected from hydrogen or $C_1$-$C_{30}$ straight or branched chain, saturated or unsaturated alkyl, aryl, or trialkylsiloxy; each R group is independently selected from hydrogen or a $C_{1-30}$ straight or branched chain, saturated or unsaturated alkyl, phenyl or aryl, trialkylsiloxy; and x and y are each integers of 1 to 1,000,000.

14. The method of claim 13, wherein R' is a C12-22 fatty alkyl.

* * * * *